United States Patent
Mitra

(10) Patent No.: US 10,175,248 B2
(45) Date of Patent: *Jan. 8, 2019

(54) METHODS OF POLYPEPTIDE IDENTIFICATION, AND COMPOSITIONS THEREFOR

(71) Applicant: Washington University, Saint Louis, MO (US)

(72) Inventor: Robi D. Mitra, Fenton, MO (US)

(73) Assignee: Washington University, Saint Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/881,931

(22) Filed: Jan. 29, 2018

(65) Prior Publication Data

US 2018/0156817 A1 Jun. 7, 2018

Related U.S. Application Data

(60) Continuation of application No. 15/390,331, filed on Dec. 23, 2016, now Pat. No. 9,880,175, which is a continuation of application No. 14/100,518, filed on Dec. 9, 2013, now Pat. No. 9,528,984, which is a division of application No. 11/674,642, filed on Feb. 13, 2007, now abandoned.

(60) Provisional application No. 60/772,997, filed on Feb. 13, 2006.

(51) Int. Cl.
G01N 33/68 (2006.01)
G01N 33/543 (2006.01)
G01N 33/58 (2006.01)

(52) U.S. Cl.
CPC ... *G01N 33/6845* (2013.01); *G01N 33/54306* (2013.01); *G01N 33/582* (2013.01)

(58) Field of Classification Search
None
See application file for complete search history.

(56) References Cited

U.S. PATENT DOCUMENTS

| | | | |
|---|---|---|---|
| 4,208,479 A | 6/1980 | Zuk | |
| 6,265,176 B1 | 7/2001 | Lin et al. | |
| 6,998,241 B2 | 2/2006 | Boga | |
| 2002/0048823 A1 | 4/2002 | Hu | |
| 2002/0123074 A1 | 9/2002 | Self et al. | |
| 2004/0248151 A1* | 12/2004 | Bacus | G01N 33/5041 435/6.14 |
| 2005/0009110 A1 | 1/2005 | Chang | |
| 2005/0164324 A1 | 7/2005 | Gygi | |
| 2007/0134685 A1 | 6/2007 | Mauro et al. | |
| 2007/0237775 A1* | 10/2007 | Kikly | C07K 16/26 424/141.1 |
| 2008/0199892 A1* | 8/2008 | Ronin | C07K 16/26 435/7.94 |

OTHER PUBLICATIONS

Cui, Y., et al, Nanowire nanosensors for highly sensitive and selective detection of biological and chemical species. Science 293: 1289-1292, 2001.
Gesellchen, F., et al., Direct optical detection of protein-ligand interactions. Methods in Molecular Biology 305: 17-46, 2005.
Jayasena, S.D., et al., Aptamers: an emerging class of molecules that rival antibodies in diagnostics. Clinical Chemistry 45: 1628-1650, 1999.
Jost, J.-P. et al., Study of protein-DNA interactions by surface plasmon resonance (real time kinetics). Nucleic Acids Research 19: 2788, 1991.
Koo, T.-W. et al., Single-molecule detection of biomolecules by surface-enhanced coherent anti-Stokes Raman scattering. Opt. Lett. 30: 1024-1026, 2005.
Kroger, K et al., Epitope-mapping of transglutaminase with parallel label-free optical detection. Biosens. Bioelectron. 17: 937-944, 2002.
Mitra, R.D., et al., Digital genotyping and haplotyping with polymerase colonies. PNAS 100: 5926-5931, 2003.
Ogawa, A., et al., Aptamer selection for the inhibition of cell adhesion with fibronectin as target. Bioorg. Med. Chem. Lett. 14: 4001-4004, 2004.
Silverman, J., et al., Multivalent avimer proteins evolved by exon shuffling of a family of human receptor domains. Nature Biotechnology 23: 1556-1561, 2005.
Yguerabide, J., et al., Resonance light scattering particles as ultrasensitive labels for detection of analytes in a wide range of applications. Journal of Cellular Biochemistry Supplement 37: 71-81, 2001.

* cited by examiner

*Primary Examiner* — Changhwa J Cheu
(74) *Attorney, Agent, or Firm* — Zackson Law LLC; Saul L. Zackson

(57) ABSTRACT

Methods are disclosed for identifying one or more proteins or polypeptides comprised by a sample. The methods comprise determining binding of each polypeptide with respect to each binding pool of a plurality of binding pools, wherein each binding pool comprises one or more probes which bind a structure comprised by a protein or polypeptide. In some aspects, polypeptides can be denatured and separated into individual polypeptide strands and immobilized on a solid support prior to determining binding of the binding pools. A protein, polypeptide or polypeptide strand can be identified by searching, in at least one database, for a protein or polypeptide sequence comprising binding pool targets either identical to or most similar to the binding pool targets comprised by the protein, polypeptide or polypeptide strand to be identified. Kits for identifying proteins, polypeptides and polypeptide strands are also disclosed.

18 Claims, 7 Drawing Sheets

Proteins with unique signatures

Proteins with unique signatures

METHODS OF POLYPEPTIDE IDENTIFICATION, AND COMPOSITIONS THEREFOR

CROSS-REFERENCE TO RELATED APPLICATIONS

This application is a Continuation of, and claims priority to U.S. Non-Provisional patent application Ser. No. 15/390,331, filed Dec. 23, 2016, which is a Continuation of, and claims priority to U.S. Non-Provisional patent application Ser. No. 14/100,518, filed Dec. 9, 2013, now U.S. Pat. No. 9,528,984, which is a Division of, and claims priority to U.S. Non-Provisional patent application Ser. No. 11/674,642, filed Feb. 13, 2007, now abandoned, which claims priority to U.S. Provisional Patent Application No. 60/772,997 filed Feb. 13, 2006. These applications are incorporated herein by reference, each in its entirety.

STATEMENT REGARDING FEDERALLY SPONSORED RESEARCH OR DEVELOPMENT

This invention was made with government support under HG003170 awarded by the National Institutes of Health. The government has certain rights in the invention.

INTRODUCTION

For many research and medical applications such as diagnosis and analysis, identifying and quantifying proteins and polypeptides in a sample can be of critical importance.

Sequences and structures of many proteins and polypeptides have been compiled in databases. Many such databases are freely available in public resources such as the internet (e.g., website of the National Institute of Health), and can be recorded in a digital medium such as a compact disk. Protein and polypeptide sequences comprised by a database can each be assigned an identity such as an accession number and, in some cases, a name which is in common usage by persons of skill in the art. For example, the proteome of an organism can be comprised by a database, and can comprise several thousand unique polypeptide sequences. In this connection, the human proteome comprises approximately 28,000 polypeptides (Science 291: 1218, 2001) while the proteome of the prokaryote *Escherichia coli* comprises approximately 4,000 polypeptides (Liang, P., et al., Physiol. Genomics 9: 15-26, 2002). In addition, databases of sequences and structures of proteins and polypeptides can also be compiled based upon considerations other than species origin, for example a database of the protein contents of a cell type, or a database of a category of protein, for example a database of kinases.

Many methods exist of isolating or separating polypeptides in a sample. For example, two-dimensional electrophoresis can resolve individual polypeptides in a mixture comprising thousands of polypeptides (O'Farrell, P. H., Journal of Biological Chemistry 250: 4007-4021, 1975). However, such procedures, by themselves, do not reveal polypeptide identity. Individual or small numbers of polypeptides comprised by a sample can be identified in some cases through analytical methods such as Western blotting using antibody probes directed against specific polypeptides. In some cases, a polypeptide that can be isolated in sufficient quantity can be identified by direct sequencing using established laboratory techniques. However, direct sequencing can be difficult, slow and expensive, and in many cases, a polypeptide to be identified can be present in a sample in an amount too low for accurate sequence determination.

SUMMARY

In view of the ongoing need for methods of identifying polypeptides, the present inventor has developed novel methods of polypeptide identification. The methods involve characterizing structural properties of a polypeptide using analytical laboratory methods, and searching a database of polypeptide sequences for a sequence of a polypeptide which shares the identified structural properties.

Accordingly, in various aspects, a method of identifying a protein or polypeptide of the present teachings includes a) determining presence or absence in the protein or polypeptide to be identified, of each binding pool target of a plurality of binding pool targets, wherein each binding pool target comprises one or more binding targets for one or more probes comprised by a binding pool; and b) identifying, in at least one database, a protein or polypeptide comprising binding pool targets most similar to those comprised by the protein or polypeptide to be identified. In some configurations, a polypeptide sequence comprising binding pool targets most similar to the binding pool targets comprised by the polypeptide to be identified can be a protein or polypeptide comprising binding pool targets identical to those comprised by the polypeptide to be identified.

For the polypeptide to be identified, determining presence or absence in the protein or polypeptide of a binding pool target comprises contacting the polypeptide with a a binding pool, wherein a binding pool comprises one or more probes. Each probe of a binding pool can recognize and bind a binding target. Binding of a binding pool comprising one or more probes to the protein or polypeptide (or absence of binding) is detected following the contacting. Detection of binding of at least one probe comprised by a binding pool leads to a determination that the protein or polypeptide to be identified comprises at least one binding target recognized by a probe comprised by the binding pool. Examples of protein or polypeptide structures which can be recognized and bound by a probe include epitopes of an antibody, a peptide motif comprising at least one amino acid up to about six amino acids, a glycosyl moiety such as an N-linked or an O-linked glycosyl moiety, a GPI anchor, a disulfide linkage, a pyroglutamic acid, a nitrotyrosine or a combination thereof. Examples of amino acids which can be recognized or contribute to a structure recognized by a probe include a phosphorylated amino acid such as phosphotyrosine, phosphoserine and phosphothreonine, a methylated amino acid, an acylated amino acid such as an amino acid comprising a farnesyl, a myristoyl, or a palmitoyl moiety, a hydroxyproline or a sulfated amino acid such as a sulfotyrosine.

Hence, in some configurations, the methods can utilize a set of at least 2 binding pools, at least about 10 binding pools, at least about 12 binding pools, at least about 15 binding pools, at least about 50 binding pools, at least about 100 binding pools, at least about 200 binding pools, or at least about 400 binding pools. In some aspects, a probe comprised by a binding pool can recognize and bind a target peptide motif comprising one amino acid, two amino acids, three amino acids, four amino acids, five amino acids, six amino acids, or greater numbers of amino acids. In some configurations, the amino acids can be contiguous, such that a probe comprised by a binding pool can recognize and bind a target peptide motif comprising two contiguous amino acids, three contiguous amino acids, four contiguous amino acids, five contiguous amino acids, six contiguous amino acids, or greater numbers of contiguous amino acids.

In various aspects of the present teachings, a probe comprised by a binding pool can be any molecule or combination of molecules which can specifically recognize and bind a structure comprised by a protein or polypeptide. Types of probes include, without limitation, antibodies, aptamers, kinases, avimers and combinations thereof. Antibodies can be monoclonal antibodies, polyclonal antibodies or combinations thereof, and aptamers can be RNA aptamers, DNA aptamers, peptide aptamers, or combinations thereof. In various aspects, each probe comprised by a binding pool can recognize and bind one structure, or in certain aspects, a probe can be degenerate, i.e., the probe can recognize bind more than one structure.

In various aspects, detection of binding of a binding pool to a polypeptide can comprise detecting a label bound directly or indirectly to at least one probe comprised by a binding pool. A label can be any label known to skilled artisans, such as, for example, a radioisotope, a chromophore, a fluorophore, a quantum dot, an enzyme and a resonance light scattering (RLS) particle.

In some configurations, a polypeptide to be identified can be contacted with the binding pools sequentially. If binding pools are contacted with the polypeptide sequentially, the same type of label can be used to reveal the binding (or absence of binding) of each binding pool, provided that probes or labels revealing probe binding are removed, destroyed, or quenched between probe applications. Accordingly, in some aspects, determining protein or polypeptide identity can comprise cycles of testing binding of each binding pool of a plurality of binding pools. A cycle can comprise contacting the protein or polypeptide with a binding pool, determining if at least one probe comprised by the binding pool binds to the protein or polypeptide, and removing or destroying any probe from the protein or polypeptide (if necessary), or removing, quenching, or destroying any signal from a probe label, using standard methods well known to skilled artisans. The protein or polypeptide can be contacted with a different binding pool upon the completion of a cycle. The process can be repeated for each binding pool in a set of binding pools. In an alternative configuration, binding pools can be differentially labeled, for example, using as labels multiple fluorophores which absorb and/or emit light at different wavelengths, so that more than one binding pool can be applied simultaneously to the protein or polypeptide, yet detected independently.

In another configuration, each binding pool can be immobilized at a different locus, e.g., in different wells of an ELISA plate or at different positions on a microarray. Aliquots comprising a protein or polypeptide to be identified can be applied to the immobilized binding pools, and binding (or absence of binding) of the protein or polypeptide to each binding pool can be determined by methods known in the art.

In various configurations of the present teachings, presence or absence of a binding pool target in a protein or polypeptide to be identified can be considered binary property, and the protein or polypeptide can be assigned a "digital signature," i.e., a number such as a unique binary number reflecting the binding pool targets comprised by the protein or polypeptide as revealed by its binding properties towards the binding pools. Furthermore, in various aspects of the present teachings, protein or polypeptide sequences comprised by a database can be characterized by the presence or absence of target structures recognized by the binding pools. For each protein or polypeptide sequence, presence or absence of a binding pool target can be considered binary property. Hence, each protein or polypeptide can be assigned a "digital signature," i.e., a unique number such as a unique binary number reflecting the binding pool targets comprised by the protein or polypeptide. Accordingly, in various aspects of the present teachings, identification of a protein or polypeptide can comprise searching the digital signatures of the proteins or polypeptides comprised by the database for the protein or polypeptide having a digital signature most similar to that of the protein or polypeptide to be identified. In various aspects, a digital signature of a protein or polypeptide from the database can be identical to that of the protein or polypeptide to be identified (an "exact match"). However, if no exact match is found in the database to the digital signature of the protein or polypeptide to be identified, the protein or polypeptide sequence whose digital signature, when expressed as a binary number, has the shortest Hamming distance to that of the protein or polypeptide to be identified can provide the identity of the polypeptide.

In some aspects of the present teachings, methods include methods of identifying one or more proteins or polypeptides in a sample. These methods include separating the proteins or polypeptides in a sample from one another using standard methods known in the art, such as, for example, 2-dimensional gel electrophoresis in which proteins or polypeptides can be revealed as spots on a gel or membrane, and contacting the separated proteins or polypeptides with the binding pools. Binding or absence of binding of each binding pool can be determined for each polypeptide to be identified and the identities of the proteins or polypeptides can be determined by reference to a database of proteins or polypeptides, as described herein.

Aspects of the present teachings also encompass methods of determining the protein or polypeptide strand content of a sample. These methods comprise immobilizing, on a solid support, individual protein or polypeptide strands comprised by the sample, such that each polypeptide strand to be analyzed is separated by an optically resolvable distance from other protein or polypeptide strands comprised by the sample. For each protein or polypeptide strand to be analyzed, the presence or absence of binding pool target can be determined using a plurality of binding pools, and a protein or polypeptide sequence comprising binding pool targets most similar to binding pool targets determined to be comprised by the protein or polypeptide strand to be analyzed is identified as described above for individual proteins and polypeptides. In addition, in some aspects, the protein or polypeptide strands in a sample comprising an identical profile of binding pool targets can be quantified by summing the protein or polypeptide strands comprising the same profile of binding pool targets. Hence, these aspects afford both relative and absolute quantification of protein or polypeptide strands comprising a sample. In some configurations of these aspects, the methods can further include denaturing the proteins or polypeptides comprised by a sample into individual polypeptide strands. In addition, immobilizing the strands on a solid support can comprise, in various aspects, contacting the strands with a reactive moiety which covalently binds the strands to the solid support. Furthermore, In addition to, or instead of covalent binding of a protein or polypeptide strand to a support, immobilizing the strands can comprise coating the surface of the solid support with a porous gel.

In other aspects of the present teachings, methods are disclosed for identifying one or more proteins or polypeptides in a mixture. The methods involve contacting the mixture with a plurality of binding pools to form complexes, wherein each complex comprises a protein or polypeptide and one or more probes comprised by a binding pool, and wherein each probe comprised by a binding pool a) binds to a binding pool target comprising at least one amino acid up to about six amino acids, a glycosyl moiety of a glycopeptide or glycoprotein, a GPI anchor, a disulfide linkage, a pyroglutamic acid, a nitrotyrosine or a combination thereof; b) has an electrophoretic mobility that differs from the electrophoretic mobilities of probes comprised by other binding pools and c) is tagged with a label that differs from the labels of the other binding pools. Complexes formed can be separated from each other using standard laboratory methods such as electrophoretic and chromatographic methods. For each protein or polypeptide to be identified that is comprised by a complex, the presence or absence in the protein or polypeptide of each binding pool target can be determined by detecting labels comprised by the complex. The identity of the protein or polypeptide can then be determined by reference to a database of protein or polypeptides, as described herein.

Other aspects of the present teachings include kits comprising components for identifying one or more polypeptides in a sample. A kit of these aspects comprises a plurality of binding pools, wherein each binding pool recognizes and binds a different subset of structures comprised by a population of proteins or polypeptides.

Other objects and features will be in part apparent and in part pointed out hereinafter.

DETAILED DESCRIPTION

Figure 1:
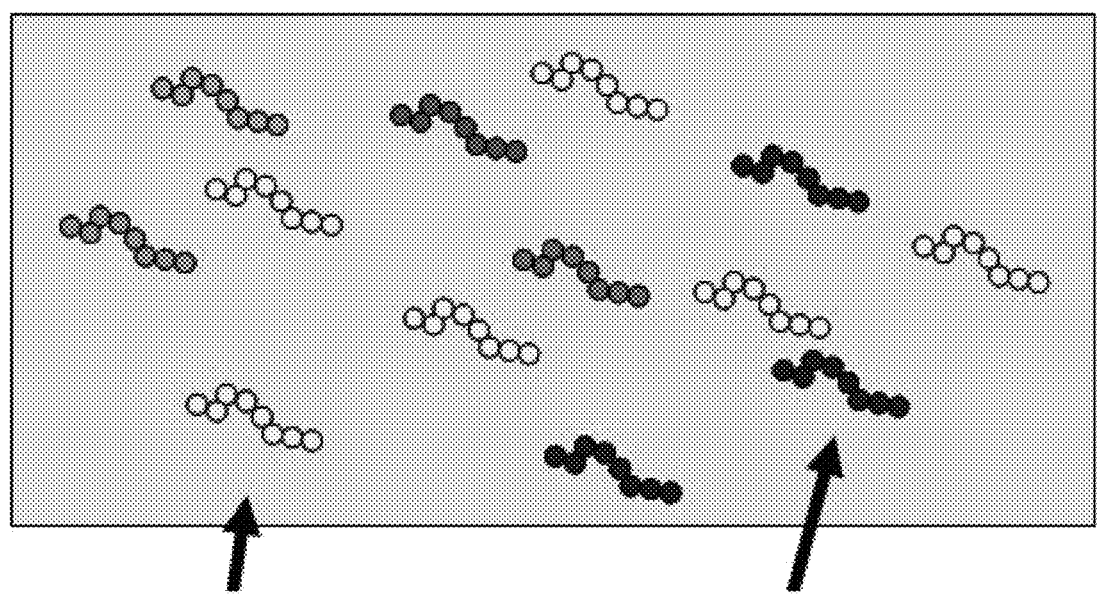
FIG. 1 illustrates digital protein analysis. Each arrow indicates a denatured protein=a linear peptide chain. A unique digital signature is assigned based on whether a spot lights up after a given binding pool is applied to the slide. (e.g. 100010001011110000111 means a protein was bound in cycle 1, 5, 9 etc.)

In various aspects, the present teachings disclose methods of identifying and quantifying a protein or polypeptide. In some configurations, a protein or polypeptide to be identified can form part of a mixture comprising other proteins or polypeptides, while in other configurations the protein or polypeptide can be substantially pure. In other aspects, the present teachings disclose methods of identifying and quantifying protein or polypeptide strands comprised by a sample. In yet other aspects, the present teachings disclose probe sets and kits for protein or polypeptide identification.

The methods and compositions described herein utilize laboratory techniques well known to skilled artisans and can be found in laboratory manuals such as: Sambrook and Russel (2006), Condensed Protocols from Molecular Cloning: A Laboratory Manual, Cold Spring Harbor Laboratory Press, ISBN 0879697717; Sambrook and Russel (2001) Molecular Cloning: A Laboratory Manual, Cold Spring Harbor Laboratory Press, ISBN 0879695773; Ausubel et al. (2002) Short Protocols in Molecular Biology, Current Protocols, ISBN 0471250929; Spector et al. (1998) Cells: A Laboratory Manual, Cold Spring Harbor Laboratory Press, ISBN 0879695226; and Harlow, E., Using Antibodies: A Laboratory Manual, Cold Spring Harbor Laboratory Press, Cold. Spring Harbor, N.Y., 1999.

In various configurations, a method of identifying a polypeptide comprises analyzing the protein or polypeptide for the presence or absence of binding pool targets for a plurality of binding pools.

The following definitions and methods are provided to better define the present invention and to guide those of ordinary skill in the art in the practice of the present invention. Unless otherwise noted, terms are to be understood according to conventional usage by those of ordinary skill in the relevant art.

As used herein, the term "probe" refers to one or more molecular species which can specifically recognize and bind a structure on a protein or polypeptide, for example a peptide target motif. Hence, a probe can be a single molecular species, such as, for example, a monoclonal antibody, or a collection of molecular species wherein each species can specifically recognize and bind the same structure. For example, a probe can comprise both an aptamer and an antibody, in which both bind the same structure such as an epitope comprised by a protein or polypeptide.

As used herein, the term "binding pool" refers to a collection of one or more probes, wherein each probe. In some aspects, a binding pool can comprise a plurality of probes, which, in the aggregate, bind to more than one structure that can be comprised by a protein or polypeptide described in a database.

As used herein, the term "polypeptide sequence" refers to a protein or polypeptide sequence comprised by a database. Accordingly, a panel of binding pools can be used to identify a protein or polypeptide as follows. A target of a binding pool (herein a "binding pool target") can comprise one or more peptide motifs and/or other structures comprised by a protein or polypeptide, such as, for example, peptide motifs comprising from one amino acid up to about six amino acids. Any individual protein or polypeptide to be identified may or may not comprise any particular binding pool target. Similarly, any protein or polypeptide comprised by a database may or may not comprise any particular structure corresponding to that of binding pool target. Conversely, a binding pool target can comprise more than one structure recognized by probes comprised by a binding pool, i.e., the probes comprised by a binding pool need not all specifically recognize the same structures. In some configurations, a binding pool can recognize multiple structures among the proteins or polypeptides of a sample or database. For example, in some configurations, probes can be selected for binding pools such that each binding pool recognizes approximately 50% of the proteins or polypeptides comprised by a database.

As used herein, reference to proteins or polypeptides comprised by a database or structures comprised by proteins or polypeptides comprised by a database refers to descriptions of such proteins, polypeptides, or structures as set forth in the database, without implying that such proteins, polypeptides, or structures are actually comprised by the database. Hence, for example, a statement that a polypeptide comprised by a database is the same as a polypeptide comprised by a sample indicates that the database describes a polypeptide comprising the same structure as the polypeptide comprised by the sample.

Accordingly, in various embodiments, if binding of a binding pool to a protein or polypeptide is considered binary (i.e., a binding pool either binds or does not bind a protein or polypeptide), then a panel of n binding pools in which each binding pool binds a different subset of binding pool targets can be used to establish $2^n$ different possible binding profiles. Stated in a different way, the minimum number of binding pool specificities required to establish unique identities for each protein or polypeptide in a database of p sequences is the integer nearest to and greater than $\log_2(p)$. For example, assuming the human proteome comprises ~30,000 polypeptides, $\log_2 30,000 \approx 14.872$, and therefore a panel of at least 15 binding pools can be used to assign a unique digital signature to each polypeptide of the human proteome. Similarly, assuming that the *E. coli* proteome comprises ~4,000 polypeptides, $\log_2 4,000 \approx 11.966$, and therefore a panel of at least 12 binding pools can be used to assign a unique digital signature to each polypeptide of the *E. coli* proteome.

Accordingly, in various aspects of the present teachings, the binding specificities of at least n probes can be used to assign a unique "digital signature" to each polypeptide comprised by a database of p polypeptide sequences, wherein n is an integer, and $n \geq \log_2 (p)$. A digital signature is a number which represents the binding pool targets comprised by a polypeptide. For example, for a binary signature, each position in the signature can be either a "1" or a "0," wherein a "1" indicates presence, and a "0" indicates absence of a binding pool target. In a hypothetical example, a panel of 15 binding pools specific for 15 different binding pool targets could be used to assign a digital signature comprising 15 digits to each protein or polypeptide comprised by a database, wherein presence or absence of each binding target sequence motif is designated by a different position in the binary signature. A binary signature for a polypeptide sequence such as 100110110010111 would indicate that the polypeptide sequence comprises the target sequence motifs for 9 of the 15 binding pools (i.e., those designated by numeral "1"), and does not comprise the target sequence motifs for 6 of the 15 binding pools (i.e., those designated by numeral "0"). To identify an unknown protein or polypeptide, the protein or polypeptide to be identified can be assigned a digital signature based upon the binding specificities of each of the 15 binding pools. A comparison of the digital signature of the protein or polypeptide to be identified with the digital signatures of proteins or polypeptide comprised by a database will reveal the protein or polypeptide sequence having a digital signature closest to that of protein or polypeptide to be identified. If the digital sequence of the protein or polypeptide to be identified is identical to that of a protein or polypeptide comprised by a database, the identity of the protein or polypeptide is established. If no protein or polypeptide has a digital signature identical to that of the protein or polypeptide to be identified, then the digital signature of the protein or polypeptide closest to that of the polypeptide to be identified can provide the identity of the polypeptide. In some configurations, if the digital signatures of the proteins or polypeptides comprised by a database and the protein or polypeptide to be identified are binary numbers, the protein or polypeptide sequence closest to that of the protein or polypeptide to be identified can be the protein or polypeptide having a digital signature with the minimum Hamming distance to that of the protein or polypeptide to be identified, wherein "Hamming distance" is defined as the number of positions in two numerical strings of equal length for which the corresponding elements are different. In various aspects, the digital signature of the protein or polypeptide sequences of a database can be determined with respect to a set of binding pool targets using routine methods such as in silico analysis. This determination can be made either prior to or following analysis of the binding profile of a protein or polypeptide to be identified with respect to a set of binding pools.

Hence, in various aspects, the present teachings disclose methods of identifying a protein or polypeptide. The methods comprise determining, in the protein or polypeptide to be identified, presence or absence of each binding pool target of a plurality of binding pool targets. In these aspects, each binding pool target can be a binding target for at least one probe comprised by a binding pool, and can comprises at least one amino acid up to about six amino acids. In various aspects, the methods further comprise identifying, in at least one database, a protein or polypeptide comprising binding pool targets most similar to the binding pool targets comprised by the protein or polypeptide to be identified. In various aspects, the protein or polypeptide comprising binding pool targets most similar to those comprised by the protein or polypeptide to be identified the binding pool targets comprised by the polypeptide to be identified.

In some configurations, determining, in the protein or polypeptide to be identified, the presence or absence of binding pool targets can comprise contacting the protein or polypeptide with binding pools which each bind a binding pool target. For each binding pool, binding of at least one probe comprised by the pool to a binding target can be detected if the target is comprised by the protein or polypeptide to be identified.

In various aspects, the plurality of binding pools can be a panel of binding pools comprising at least n probes, wherein $2^n$ is greater than or equal to the number of protein or polypeptide sequences comprised by a database of protein or polypeptides. Accordingly, in various configurations, a panel of binding pools can comprise at least 2 binding pools, at least about 10 binding pools, at least about 12 binding pools, at least about 15 binding pools, at least about 16 binding pools, at least about 18 binding pools, at least about 20 binding pools, at least about 50 binding pools, at least about 100 binding pools, at least about 200 binding pools, or at least about 400 binding pools. While the present methods can be practiced with any number of binding pools greater than the minimum required for the proteome or other grouping comprising the sequence of the protein or polypeptide to be identified, in some configurations, a panel of binding pools can comprise up to about 400 probes, up to about 200 probes up to about 100 probes, or up to about 50 probes.

In various configurations, a probe comprised by a binding pool can bind a peptide motif of from one amino acid up to about 6 amino acids, or more complex structures comprising amino acids. Hence, in various aspects of the present teachings, a probe can recognize and bind a target structure such as, without limitation, a single amino acid, a peptide up to about six amino acids, a glycosyl moiety of a glycopeptide or a glycoprotein, a GPI anchor, a disulfide linkage, a pyroglutamic acid, a nitrotyrosine and a combination thereof. A single amino acid recognized by a probe can be, without limitation, a phosphorylated amino acid, a methylated amino acid, an acylated amino acid, a hydroxyproline or a sulfated amino acid. A phosphorylated amino acid can be, for example, a phosphoserine, a phosphotyrosine, or a phosphothreonine. Accordingly, in various aspects, the present methods can be practiced using any probes which can specifically recognize and bind a structure found on a subset of proteins or polypeptides comprising a database. In various aspects, probes can be combined to establish binding pools. Non-limiting examples of probes which can be used include antibodies, aptamers (Jayasena, S. D., et al., Clinical Chemistry 45: 1628-1650, 1999), kinases, avimers (Silverman, J., et al., Nature Biotechnology 23: 1556-1561, 2005) and combinations thereof. In various aspects, a molecular species which can contribute to or function as a probe can have a dissociation constant Kd for its binding target of less than about $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, $10^{-15}$ M or lower.

In some aspects, a probe can comprise a monoclonal or polyclonal antibody against a target structure found in a protein or polypeptide. Monoclonal and polyclonal antibodies can be generated using standard techniques known in the art (see generally, Carter (2006) Nat Rev Immunol 6(5), 343-357; Teillaud (2005) Expert Opin Biol Ther. 5 (Supp. 1) S15-27; Subramanian, ed. (2004) Antibodies: Volume 1: Production and Purification, Springer, ISBN 0306482452; Lo, ed. (2003) Antibody Engineering Methods and Protocols, Humana Press, ISBN 1588290921; Ausubel et al., ed. (2002) Short Protocols in Molecular Biology 5th Ed., Current Protocols, ISBN 0471250929; Brent et al., ed. (2003) Current Protocols in Molecular Biology, John Wiley & Sons Inc, ISBN 047150338X; Coligan (2005) Short Protocols in Immunology, John Wiley & Sons, ISBN 0471715786; Sidhu. (2005) Phage Display In Biotechnology and Drug Discovery, CRC, ISBN-10: 0824754662). Furthermore, antibodies have been produced against short peptides (e.g., Kuriyama, R., et al., Cell Motility and the Cytoskeleton 30: 171-182, 1995 (antibodies against dipeptides); Vassilev, T. L., et al., Blood 93: 3624-3631, 1999 (antibodies against tripeptides)) and single amino acids (e.g., Frackelton, A. R., et al., Journal of Biological Chemistry 259: 7909-7915, 1984 (antibodies against phosphotyrosine). In various aspects, a probe such as an antibody can bind to an epitope comprised by a protein or polypeptide. The epitope can involve amino acid residues that are contiguous or non-contiguous in a protein or polypeptide chain.

In various configurations, probes which recognize and bind specific structures comprised by proteins or polypeptides can be generated using standard methods well known to skilled artisans. In non-limiting example, antibodies against a peptide of a sequence known to be comprised by a protein comprised by a database can be produced by immunizing an animal such as a mouse or a rabbit with the peptide. The peptide itself can be synthesized using standard techniques, such as chemical synthesis methods or molecular cloning techniques known to skilled artisans. In some aspects, such peptides can be incorporated into larger polypeptides to enhance immunogenicity. In non-limiting example, to generate an antibody, an immunogen comprising a random copolymer of amino acids plus a dimer motif can be introduced into a host animal such as a rabbit. Serum from the inoculated animal can be collected and used as a polyclonal antibody probe. In some aspects, an antibody which specifically binds a dimer motif can be affinity-purified using well-known techniques.

Similarly, in various aspects of the present methods, aptamers can be used as probes contributing to a binding pool. Aptamers can be produced against specific peptide motifs using standard techniques, such as, for example, those described in Ogawa, A., et al., Bioorg. Med. Chem. Lett. 14: 4001-4004, 2004; and Jayasena, S. D., Clinical Chemistry 45: 1628-1650, 1999. In various configurations, an aptamer can be, without limitation, an RNA aptamer, a DNA aptamer or a peptide aptamer.

In some aspects, a probe which can be used in a binding pool in the methods described herein can be a probe that not only can recognize and bind a structure comprised by one or more proteins or polypeptides, but can do so reversibly, i.e., the probe can be removed from a protein or polypeptide comprising the probe's target structure following detection of binding of the probe to the polypeptide (see below).

Detection of binding of a binding pool to a protein or polypeptide can comprise, in various aspects of the present teachings, detection of a label which is attached directly or indirectly to a probe comprised by the binding pool. Non-limiting examples of labels which can be used include moieties directly attached to a probe such as, without limitation, radioisotopes, chromophores, fluorophores, enzymes such as horseradish peroxidase or alkaline phosphatase, quantum dots and resonance light scattering particles (Yguerabide, J., et al., Journal of Cellular Biochemistry Supplement 37: 71-81, 2001). In some configurations, a label can be bound indirectly to a probe, for example, a secondary antibody tagged with a fluorophore if the probe comprises a primary antibody. In some aspects, binding (or absence of binding) between a polypeptide to be identified and a binding pool can be detected using detection methods that do not require a separate label, such as, for example, surface plasmon resonance (SPR) and reflectometric interference spectroscopy (RIFS) (Gesellchen, F., et al., Methods in Molecular Biology 305: 17-46, 2005). In some configurations, a label can be one which can be removed, destroyed or quenched after it is detected, using techniques well known to skilled artisans. For example, in some configurations, a fluorophore can be bleached by intense irradiation with excitation wavelengths of light.

In some aspects, to determine the digital signature of a protein or polypeptide to be identified, binding pools can be applied sequentially to the protein or polypeptide. In some aspects, the protein or polypeptide to be identified can be immobilized on a solid support using standard techniques well known to skilled artisans. In these aspects, a first binding pool can be contacted with the immobilized protein or polypeptide, and binding (or lack of binding) between the binding pool and the protein or polypeptide can be determined by detecting the presence or absence of a label, for example using a fluorescence detector such as a fluorimeter or a fluorescence microscope, or by detection of unlabelled probe using, for example, SPR or RIFS. The binding pool can then be removed from the immobilized polypeptide (if necessary) by methods well known to skilled artisans, such as, for example, by contacting the complex formed between the protein or polypeptide to be identified and the binding pool with a buffer known to disrupt antibody-antigen complexes, such as, in non-limiting example, 0.1 M glycine-HCl, pH 2.5-3.0; ImmunoPure® IgG Elution Buffer (Pierce Biotechnology, Inc, Rockford, Ill.) or ImmunoPure® Gentle Ag/Ab Elution Buffer (Pierce Biotechnology). This process can then be repeated for each binding pool of a set of binding pools, until a complete binding profile of the polypeptide with respect to the binding pools is determined. In various configurations, a digital signature such as a binary digital signature of the protein or polypeptide to be identified can be determined using the binding data from the binding pool.

In related aspects, determination of the digital signature of a protein or polypeptide to be identified can involve simultaneous binding of more than one binding pool, provided the binding pools can be distinguished. In these aspects, the number of binding pools which can be applied simultaneously to a protein or polypeptide to be identified can be the number of binding pools which can be detected independently, although it is always possible that simultaneous binding to two or more motifs comprised by the same protein or polypeptide could be subject to steric interference. Nonetheless, binding pool labels which can be used to differentially detect binding pools include, in non-limiting example, fluorophores and quantum dots having different excitation and/or emission wavelengths.

In other related aspects, determination of the digital signature of a protein or polypeptide to be identified can involve simultaneous binding of more than one binding pool, wherein each binding pool is immobilized at an individual locus on a solid support, such as, for example, wells of an ELISA plate or loci on a microarray. In these aspects, a sample comprising the protein or polypeptide to be identified can be aliquoted and contacted with each binding pool of a binding pool set. Routine methods known to skilled artisans can then be used to determine which binding pools bind the polypeptide. Such methods include, for example, surface plasmon spectroscopy (Jost et al., Nucleic Acids Research 19: 2788, 1991), silicon nanowire sensing (Cui, Y., et al. Science 293: 1289-1292, 2001), hapten tagging, flurophore tagging, radioisotope tagging, quantum dot tagging, RLS particle tagging, or loss of binding of a secondary probe in a competitive binding assay.

In various aspects of the present teachings, a protein or polypeptide to be identified can be denatured. It is expected that denaturation can, in some cases, expose a structure in a protein or polypeptide which would otherwise be inaccessible to a probe. Denaturation can include contacting the protein or polypeptide with one or reducing agents such as, for example, β-mercaptoethanol, dithiothreitol, or a combination thereof. Denaturation can also further comprise contacting the probe or polypeptide with at least one chaotrope, detergent or other denaturant such as, for example, urea, guanidinium chloride, or sodium dodecyl sulfate (SDS). In some aspects, denaturation can also comprise heating the protein or polypeptide. Accordingly, in some configurations a protein or polypeptide to be identified can be heated in the presence of SDS and β-mercaptoethanol. In configurations in which the protein or polypeptide is immobilized on a solid support, the denaturation can be effected either prior to or subsequent to the immobilization.

In various aspects of the present teachings, a database can be a collection of any number of proteins or polypeptides. For example, a database can comprise a proteome of at least one eukaryotic or prokaryotic species, and can be, in some configurations, a database comprising at least about 90% of the polypeptide sequences encoded by the genome of a species. In some aspects, a proteome can be a eukaryotic or prokaryotic proteome. For example, a proteome can be a vertebrate proteome such as a mammalian proteome, such as, in non-limiting example, a human proteome. In other examples, a proteome can be a prokaryotic proteome such as an E. coli proteome. The protein or polypeptide sequences comprised by a proteome database can include sequences determined by conceptual translation of predicted open reading frames of a genome, conceptual translation of mRNA sequences, and/or actual sequence data of proteins and polypeptides that have been directly sequenced. A database can be, in some configurations, limited to protein or polypeptide sequences of the proteome of a single species, or, in alternative configurations, can comprise polypeptide sequences of proteomes of multiple sequences, for example, a combination of human and mouse proteomes. In non-limiting example, a database can be a RefSeq protein database, available from the website of the National Institute of Health. In various aspects, a database which can be used with the methods described herein can be a database of protein or polypeptide sequences or structures selected on any rationale. In non-limiting examples, a database can be assembled from known sequences of kinases or nucleases, from structures of proteins known to be expressed by muscle cells, from sequences expressed by a bacterial pathogen, or structures of proteins comprised by a plant. In addition, in some configurations, databases can be combined to form larger databases. In non-limiting example, a database can comprise all known sequences of proteins expressed in mammalian cells.

In some configurations of the present teachings, methods are disclosed for identifying two or more proteins or polypeptides in a sample. These methods comprise separating the proteins or polypeptides in the sample, and identifying each polypeptide to be identified by the methods disclosed for a single protein or polypeptide. In various aspects, separation of the polypeptides can be effected by methods known to skilled artisans, such as, for example, electrophoresis, chromatography, or a combination thereof. The separation can be followed by immobilization of the separated polypeptides. In non-limiting example, the separation and immobilization can comprise separating the polypeptide by gel electrophoresis (such as SDS-polyacrylamide gel electrophoresis (SDS-PAGE), or a 2-dimensional electrophoresis combining isoelectric focusing and SDS-PAGE) and transferring the proteins or polypeptides in the gel onto a solid support such as a nitrocellulose or nylon membrane, using techniques well known to skilled artisans. In various aspects, the transferred polypeptides can be immobilized by adsorption or attachment of the proteins or polypeptides to the membrane.

In some configurations of the present teachings, methods are disclosed for determining the polypeptide strand content of a sample. As used herein, the term "polypeptide strand" refers to a single polypeptide chain, as distinct from the term "polypeptide," which refers to a any number of individual polypeptide chains of the same molecular species.

Hence, in various aspects of the present teachings, methods of determining the polypeptide strand content of a sample include immobilizing, on a solid support, the polypeptide strands comprised by the sample, such that each polypeptide strand to be analyzed is separated by an optically resolvable distance from other polypeptide strands comprised by the sample. Presence or absence of each binding pool target recognized by a set of binding pools, can then be determined for each polypeptide strand, as described above. In various aspects, a digital signature can then be assigned to each polypeptide strand. Using standard methods well known to skilled artisans, the digital signatures of each polypeptide strand can then be compared to those of a database of polypeptide sequences as described above, thereby providing qualitative identification of each strand. Accordingly, identification of a polypeptide strand can comprise identifying a polypeptide comprising binding pool targets most similar to the binding pool targets comprised by the polypeptide strand to be identified. As described above, in various aspects, a database can be searched to identify a polypeptide having a digital signature identical to that of the polypeptide strand to be identified. In some aspects, if a database search reveals no polypeptide with a digital signature identical to that of the polypeptide strand to be identified, a polypeptide within the having the shortest Hamming distance to the polypeptide strand to be identified can be used to identify the polypeptide strand.

In some aspects of the present teachings, polypeptide strand content of a sample can be quantified by summing all of the digital signatures that are the same in a sample of polypeptide strands. In some aspects, the quantification can be presented in any format that an investigator finds convenient, such as, for example a histogram wherein the height of any column is proportional to the number of polypeptide sequences sharing the same digital signature. In various aspects, binding of a probe to a polypeptide strand can be detected by any known detection method that can reveal the presence of a probe-target complex, such as, in non-limiting example, surface-enhanced Raman scattering (SERS), coherent anti-Stokes Raman scattering surface plasmon resonance (SPR) or reflectometric interference spectroscopy (RHS) (Koo et al., Opt. Lett. 30: 1024-1026, 2005; Gesellchen, F., et al., Methods. Mol. Biol. 305:17-46, 2005; Kroger, K., et al., Biosens. Bioelectron. 17: 937-944, 2002), or any method which can be used to detect a label, bound directly or indirectly to probes comprising a binding pool. In some aspects, the label can be one which is detectable even if attached to only a single molecule. In non-limiting example, the label can be a fluorophore such as, for example, Cy3 or Cy5 (Invitrogen Corporation, Carlsbad Calif.), a quantum dot (Invitrogen Corporation, Carlsbad Calif.), or a resonance light scattering (RLS) particle (Genicon Sciences, San Diego, Calif.) attached directly to a binding pool. In other aspects, indirect labeling can be used, in non-limiting example, the label can be a fluorophore, quantum dot or RLS particle attached to a secondary antibody which, in turn, can bind a probe comprised by a binding pool. In yet other aspects, enzymes can be used as probes. In a non-limiting example, one or more kinases can contribute to a binding pool for the identification of kinase substrates comprised by a sample.

In various aspects, separation of polypeptide strands by an optically resolvable distance can comprise diluting (or concentrating) a sample by standard methods, and applying the sample to a solid support, such as, for example, a glass or non-fluorescent plastic microscope slide. Polypeptide strands in these aspects can also be denatured, as described above. In some aspects, the polypeptide strands can be immobilized on a solid support using materials and methods well known to skilled artisans, such as, for example, adsorption, covalent cross-linking of the polypeptide strands to the support with a chemical cross-linker such as a cross-linker available from Pierce Biotechnology, Inc, Rockford, Ill., or application to the support of a porous medium such as an agarose or polyacrylamide gel, FOR example as described in Mitra, R. D., et al., Proceedings of the National Academy of Sciences 100: 5926-5931, 2003. As used herein, an "optically resolvable distance" is a distance great enough that two neighboring objects such as neighboring polypeptide strands or labeled probes bound to the strands can be distinguished from each other using optical microscopy. In various aspects, an optically resolvable distance can be at least about 0.5 micron, at least about 1 micron, at least about 5 microns, or greater. In various aspects, two or more polypeptide strands which are closer than the minimum optically resolvable distance can be considered to overlap and can be excluded from further analysis.

The present teachings also include, in some aspects, kits for use in identifying proteins, polypeptides or polypeptide strands. A kit of these aspects can comprise a plurality of binding pools wherein each binding pool comprises one or more probes, wherein each probe can recognize and bind a structure comprised by a protein or polypeptide, as described above. A kit of these aspects can comprise at least about 5 binding pools, at least about 10 binding pools, at least about 12 binding pools, at least about 15 binding pools, at least about 20 binding pools, at least about 50 binding pools, at least about binding pools, or at least about 200 binding pools. In various aspects, each binding pool comprised by the kit can recognize and bind one or more structures in proteins or polypeptides described in a database, as described above. In some aspects, a probe comprised by the kit can further comprise at least one probe label, as described above. In other aspects, the kit can further comprise at least one secondary probe comprising an optically detectable label, such as, in non-limiting example, a fluorescently-tagged secondary antibody.

In addition, in some aspects, a kit can further comprise at least one reducing agent such as β-mercaptoethanol or dithiothreitol, and, in some configurations, a denaturant such as urea, guanidinium chloride or sodium dodecyl sulfate.

In yet other aspects, a kit can further comprise additional materials for analyzing polypeptides or polypeptide strands. These materials can include, in non-limiting example, a solid support such as glass or plastic microscope slides, ELISA plates, microarrays (including ELISA plates or arrays with probes already immobilized at identified loci), a computer-readable compact disk comprising a database of protein or polypeptide structures, and instructions.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention, and are not intended to limit the scope of the claims. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention. The description of a composition or a method in an example does not imply that a described composition has, or has not, been produced, or that a described, method has been performed, irrespective of verb tense used.

Example 1

This example provides an overview of digital polypeptide strand analysis.

As illustrated in FIG. 1, proteins and polypeptides comprised by a sample are denatured and linearized by heating in the presence of β-mercaptoethanol and sodium dodecyl sulfate. The released strands are then immobilized on a microscope slide, such that single polypeptide strands are 1) optically resolvable and 2) accessible to binding by probes. Binding pools, each of which is labeled with a tag such as a quantum dot and binds a structure known to be comprised by at least one protein or polypeptide of a refseq database, are applied to the sample sequentially, following a cycle of binding, washing, detecting, and eluting. Accordingly, a first binding pool comprising a plurality of probes is applied to the surface, excess probe is removed by washing, and binding between the first binding pool and each polypeptide strand is then determined using a fluorescence microscope. Probes hound to polypeptide strands on the slide are then removed using an elution buffer. The process is repeated for each of the binding pools. Based upon the results of the binding pool binding assays, digital signatures are assigned to each polypeptide strand (FIG. 1). Polypeptides can then be quantified by counting the number of polypeptide strands having the same digital signatures, and identity of polypeptide strands can be determined by comparing their digital signatures to those of polypeptide sequences comprised by the refseq database.

Example 2

This example illustrates methods of designing binding pools that will uniquely identify most polypeptides in a refseq database.

Using the twenty standard amino acids found in polypeptides and coded for by the genetic code, there are 400 possible 2-amino acid motifs. One possible set of probes comprises probes against every possible 2-amino acid motifs. Accordingly a weight matrix of the form NNNNNGANNNNN was used as a starting point, since the average 2 amino acid motif hits ~½ of the polypeptides in the refseq database (average=0.505, st. dev=0.1746). Duplicate polypeptides were removed. Following the removal, 27,910 distinct polypeptides remained in the database. Notably, 7,737 of the polypeptides contain an alternatively spliced isoform somewhere in the database. These alternatively spliced isoforms were left in the analysis.

A. 400-bit-long digital signature for each polypeptide in the database was then determined. The number of polypeptides with unique signatures in the database was then computed. It was found that 26,537 of the 27,910 polypeptides had unique signatures. Therefore, 95% of the polypeptides could be uniquely identified, including the vast majority of alternatively spliced isoforms.

Not trying to distinguish splice forms, it was found that 27,839 of the 27,910 polypeptides had unique signatures. Therefore, 99.7% of the polypeptides comprised by the database could be uniquely identified.

Example 3

Figure 2:
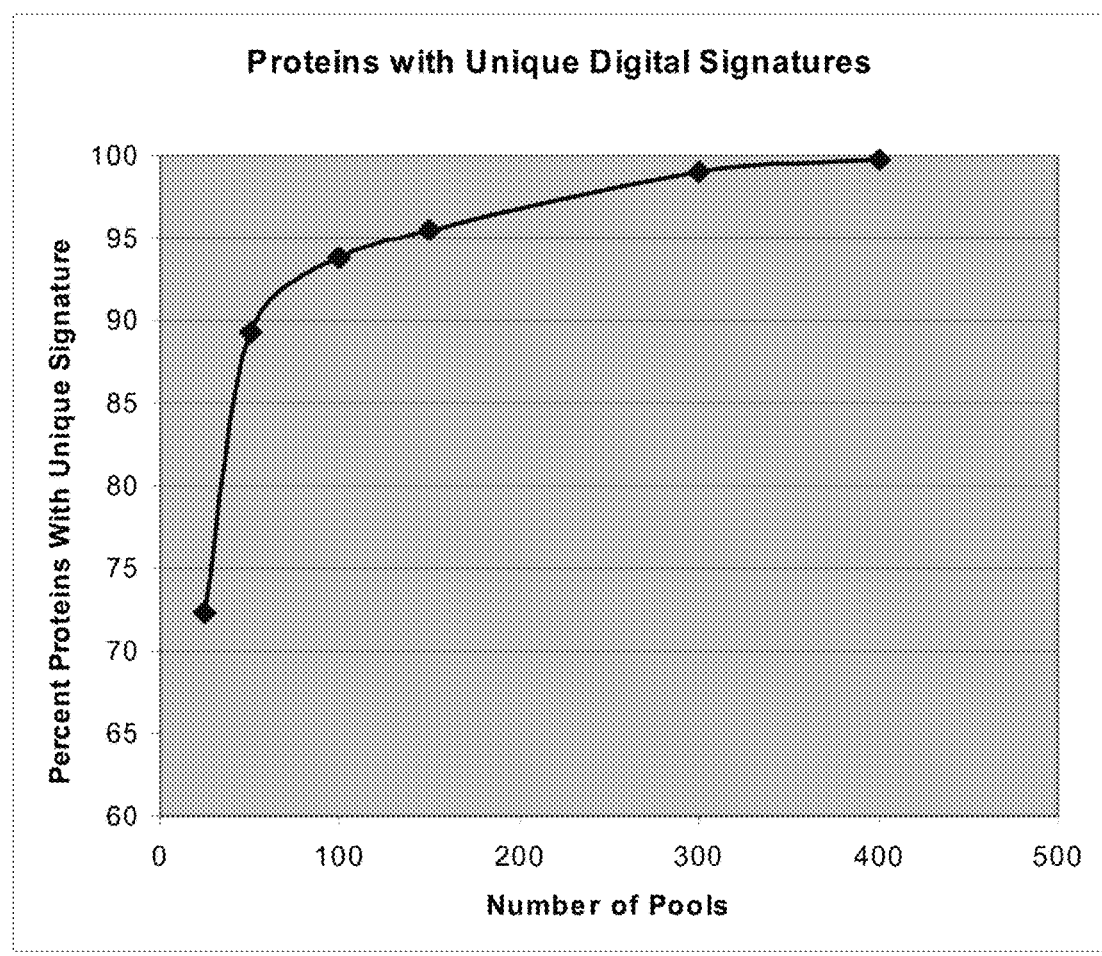
FIG. 2 illustrates percentage of polypeptides with unique digital signatures as a function of the number of randomly selected 2-amino acid probes.

This example illustrates methods of designing probes that will uniquely identify most polypeptides in the refseq database using smaller numbers of probes compared to Example 2. In this example, 25, 50, 100, 150, or 300 of the 400 di-amino acid pools used in Example 2 were randomly selected and then the question was asked how many polypeptides had unique digital signatures. The results are plotted in FIG. 2. If 100 pools are randomly selected, ~93.5% of the polypeptides have unique signatures.

Figure 3A:
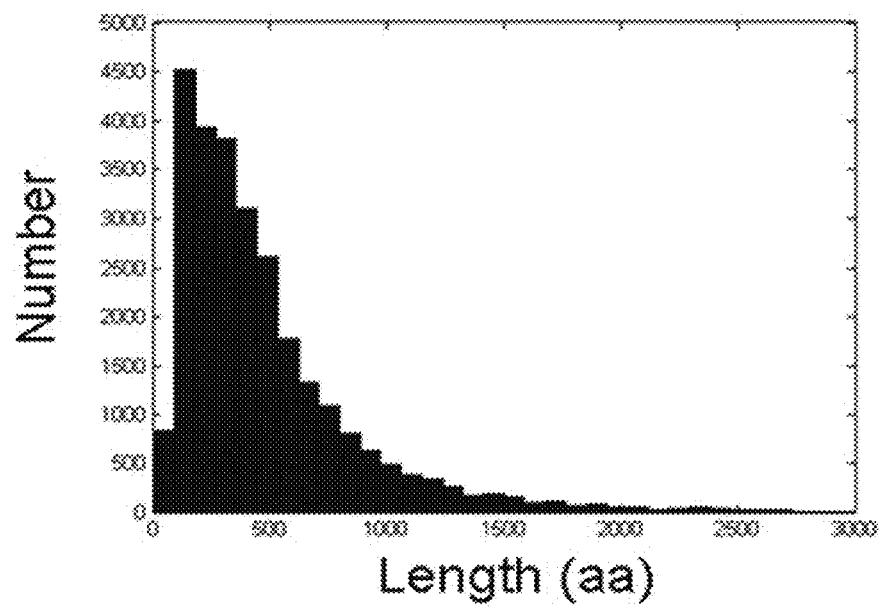
FIG. 3A-B illustrates distribution of lengths of polypeptides with unique digital signatures (FIG. 3A) and non-unique digital signatures (FIG. 3B) (Note differences in dependent axis scale).
Figure 3B:
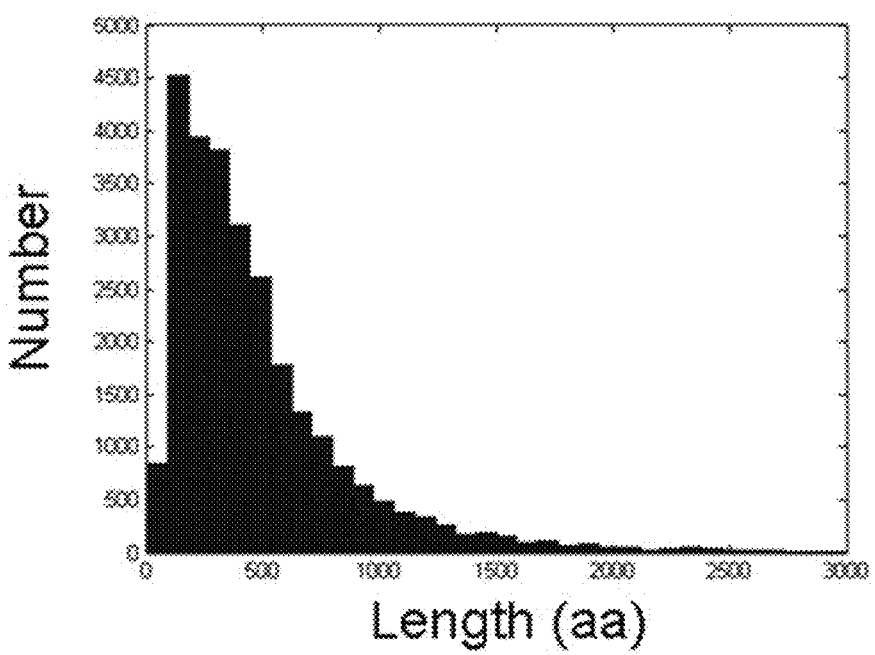

Surprisingly, most of the polypeptides that shared signatures were not splice forms of one another. It was hypothesized that polypeptides with shared signatures would tend to be long polypeptides, as they would tend to contain almost all possible 2 amino acid combinations. Therefore, it was expected that they will be harder to discriminate from one another as their signatures would tend to contain mostly 1's. A histogram plotting the frequency as a function of length is shown in FIG. 3. Indeed, polypeptides with non-unique signatures tend to be longer than polypeptides with unique signatures. This indicates that performance can be improved by including some pools with higher information content motifs.

Example 4

This example illustrates robustness of the probe selection methods with respect to errors introduced by single molecule detection and cross-reactivity of probes.

Here experimental error in generating the digital signatures is modeled to see how error would affect results. It is assumed that 5% of binding events are not detected. For example, if a binding pool were applied that should recognize and bind a GA motif, and a given polypeptide has the GA motif, it is assumed that 5% of the time, a binding event is not detected. This could occur due to reasons such as, the polypeptide is not fully denatured, or because the label is not detected. Furthermore, it is assumed that 5% of the time, a polypeptide that does not have a given motif (e.g. GA) is erroneously called as having this motif. This result from, for example, probe cross-reactivity, or simply background binding of the probe to the slide.

The experiment proceeds as follows:

1. Pick a polypeptide at random from a database and generate a digital signature.

2. Add noise to the signature by changing 1's to 0's or 0's to 1 according to the error rate (5% of the time).

3. Take this "experimental" digital signature and search the database to find the polypeptide that has a digital signature with the smallest Hamming distance to the experimental digital signature. Is this the original polypeptide? If so, score a correct call. If not, score an incorrect call.

4. Repeat steps 2 and 3 a total of 20 times. Record the fraction of correct calls for this polypeptide.

5. Go to step 1 199 more times.

Figure 4:
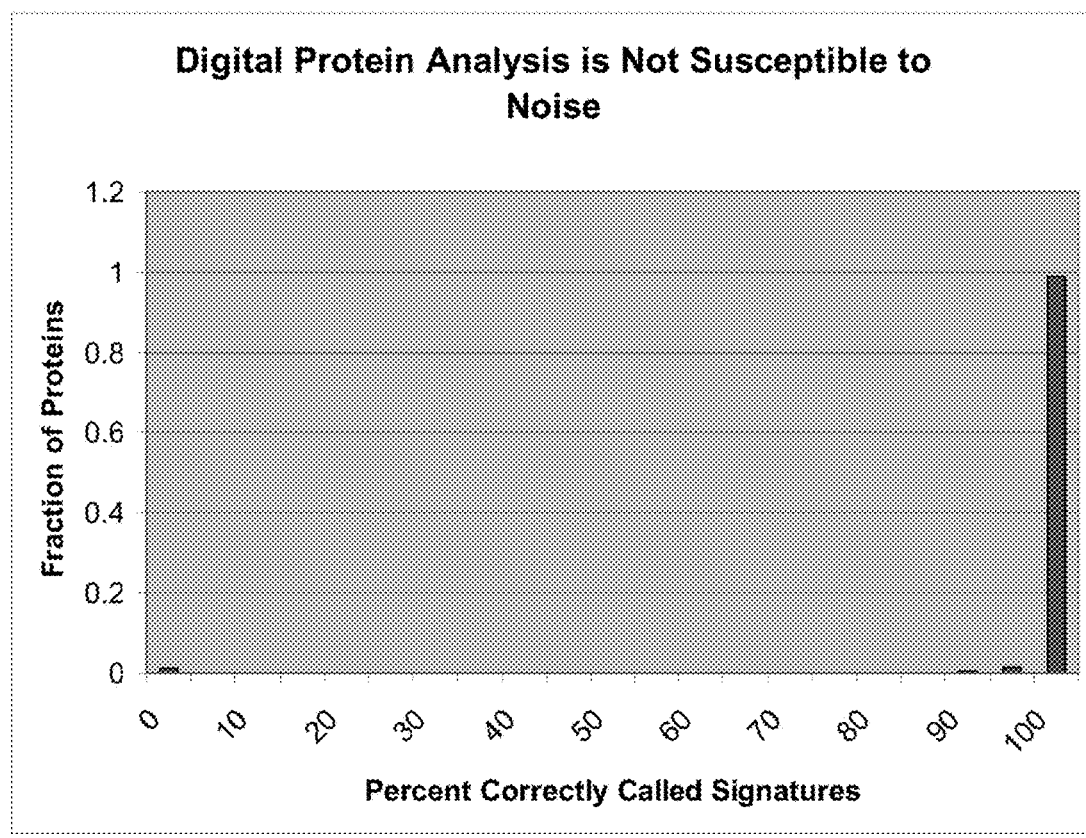
FIG. 4 illustrates a histogram showing the fraction of proteins plotted against the percent correctly called signatures after the digital signatures were corrupted with noise.

The results are plotted in FIG. 4. For 98% of the polypeptides, the correct call was made 100% of the time. Thus, this procedure is quite resistant to noise.

Example 5

This example illustrates methods of finding the optimal set of probes.

In order to develop a method of finding an optimal set of probes, a heuristic approach was taken that allows a small set of probes to be used to identify polypeptides. This approach provides the same type of coverage and resistance to noise that was achieved using the set of 400 2 amino acid motifs.

Figure 5:
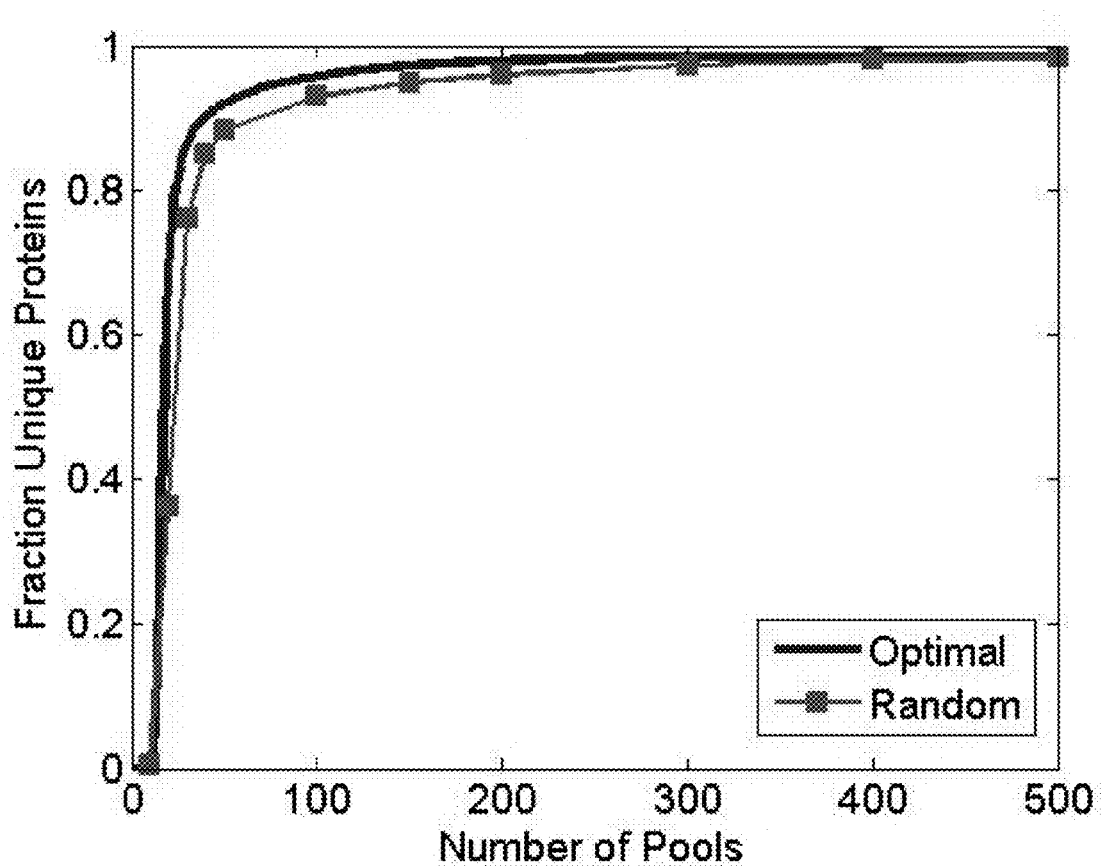
FIG. 5 illustrates the fraction of polypeptides in a refseq database with unique digital signatures as a function of the size of the optimal set, and, for comparison, the percentage of proteins with unique digital signatures for a randomly chosen set of the same size.
Figure 6:
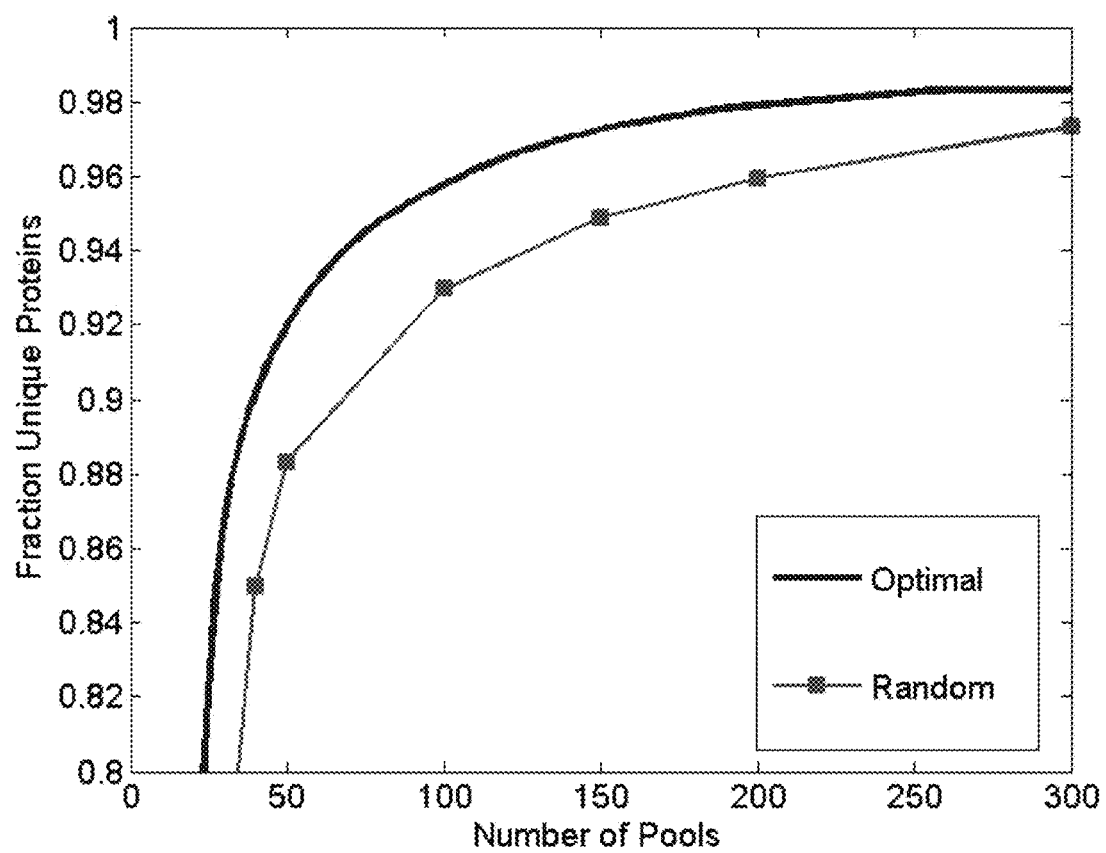
FIG. 6 illustrates an enlargement of a portion of the graph shown in FIG. 5.

The heuristic is as follows: first a set of 500 motifs was made up. This set included all 400 2 amino acid motifs, and 100 randomly sampled 3 amino acid motifs. From this set, a smaller subset of motifs was chosen that is expected to perform as well as the 400 2 amino acid motifs. To pick the first member, each motif was added to a "test set" and digital signatures are generated for each polypeptide in the refseq database. From the digital signatures, it was calculated, Ns=the effective number of unique signatures=1/(prob of picking two signatures from the dataset and having them be the same). The motif was chosen that maximized Ns, and this motif was added to the optimal set. The procedure was then repeated as before. The "test set" consisted of all motifs in the optimal set and each unselected motif. The motif that maximized Ns was again added to the optimal set. This worked well early on, but after selection of 17 motifs, the optimization was changed to optimize the actual number of unique digital signatures rather than the effective number of unique digital signatures. This was continued until all 500 motifs were used. This heuristic provides an ordering for the 500 motifs. If one wants to have an optimal motif set of 50 motifs, then the first 50 motifs can be chosen by this heuristic. In FIG. 5, the fraction of polypeptides with unique digital signatures is plotted as a function of the size of the optimal set. For comparison, the percentage of polypeptides was also plotted with unique digital signatures for a randomly chosen set of the same size. The results show that optimal pools in fact perform somewhat better than random. FIG. 6 shows an enlargement of part of the graph shown in FIG. 5, to clarify the results shown.

In theory, a database of 27,910 polypeptides could be represented by 15 probes to get unique signatures for each of them (because $2^{15}=32768$). However, polypeptides have different lengths. This implies that if a motif is going to divide a set of 50 amino acid polypeptides in half, it must have relatively low information content. But then it will not divide a set of 500 amino acid polypeptides in half, and vice versa. Therefore, it will be difficult to do much better. Still, the optimal motif set gives good results (>97% unique polypeptides) for 200 probes.

Example 6

This example illustrates resistance to noise.

The following protocol was developed to investigate resistance to noise.

1. Pick a polypeptide at random and generate an error-free digital signature.

2. Add noise to the signature by changing 1's to 0's or 0's to 1 according to the error rate (2.5% false positive (FP) and varying false negative rate).

3. Take this "experimental" digital signature and search the polypeptide database to find the polypeptide that has a digital signature with the smallest Hamming distance to the experimental digital signature. Is this the original polypeptide? If so, score a correct call. If not, score an incorrect call.

4. Repeat step 2 and 3 20 times. Record the fraction of correct calls for this polypeptide.

5. Go to step 1 199 more times.

Figure 7:
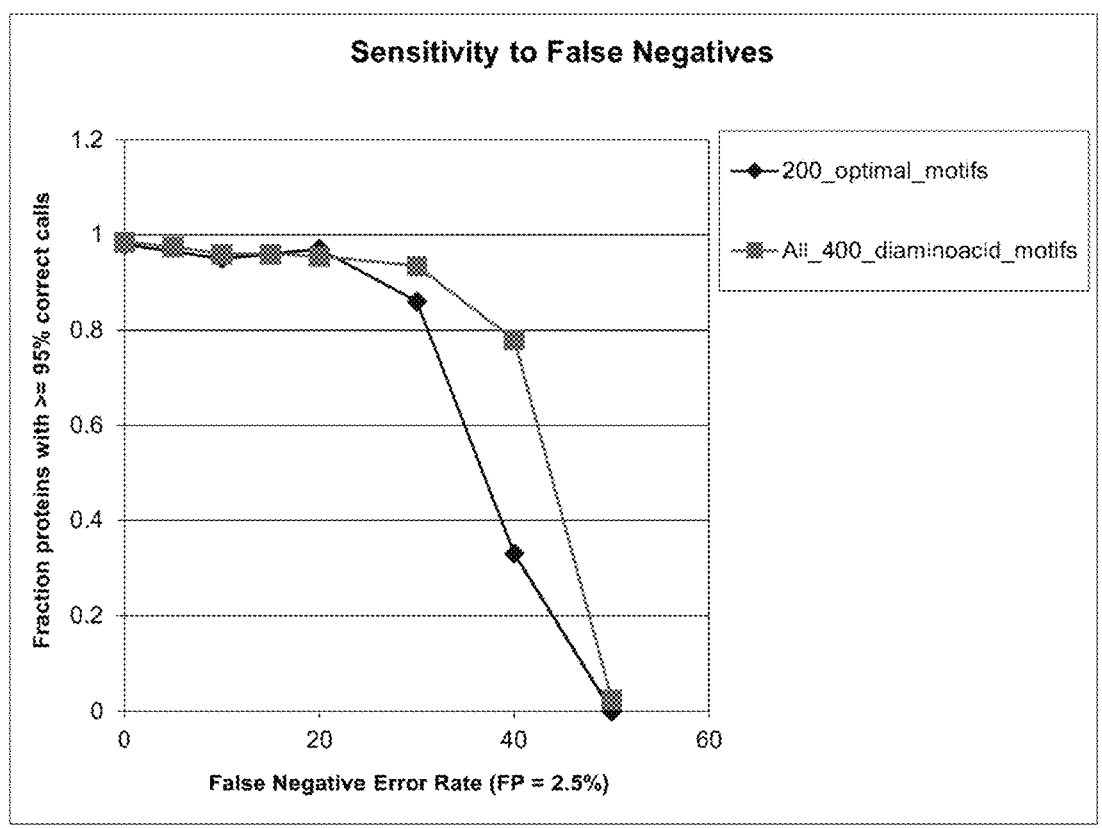
FIG. 7 illustrates sensitivity to false negatives for probes for 200 optimal 2-amino acid motifs and a full set of 400 2-amino acid motifs.

This procedure was performed using the 200 optimal motifs, and the full set of 400 diaminoacid motifs. The results are plotted in FIG. 7.

The results are good for both cases up to a 20% false negative rate. If the false negative rate is between 20 and 30%, the full set of 400 amino acids can be used. For false negative rates greater than 30%, neither set will give good results.

It is to be understood that while some of the examples and descriptions may include some conclusions about the way the disclosed methods may function, the inventor does not intend to be bound by those conclusions, but puts them forth only as possible explanations.

It is to be further understood that specific embodiments of the present teachings as set forth herein are not intended as being exhaustive or limiting, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

All publications, patents, patent applications and other references cited in this application are herein incorporated by reference in their entirety as if each individual publication, patent, patent application or other reference were specifically and individually indicated to be incorporated by reference.

What is claimed is:

1. A method of identifying a polypeptide strand, the method comprising:
   immobilizing, on a solid support, a plurality of polypeptide strands comprised by a sample, such that each polypeptide strand to be identified is separated by an optically resolvable distance from other polypeptide strands comprised by the sample;
   determining presence or absence, in a polypeptide strand to be identified, of each binding pool target of a plurality of binding pool targets; and
   identifying, in at least one database, a protein or polypeptide comprising binding pool targets most similar to the binding pool targets comprised by the polypeptide strand to be identified,
   wherein determining the presence or absence of each binding pool target of a plurality of binding pool targets is performed for each polypeptide strand to be identified;
   wherein each binding pool target is a binding target for one or more probes comprised by a binding pool, and
   wherein at least one of said binding pool targets comprises a single amino acid and at least one of said probes binds to said single amino acid in said binding pool target.

2. The method of claim 1, wherein the solid support comprises (i) a reactive moiety which covalently binds the polypeptide strands and/or (ii) an optically transparent medium selected from the group consisting of glass and non-fluorescent plastic.

3. The method of claim 1, wherein immobilizing the polypeptide strands comprises (i) covalently coupling the polypeptide strands to the solid support and/or (ii) contacting the polypeptides with a surface of the solid support, and coating the surface with a porous gel.

4. The method of claim 1, further comprising quantifying the polypeptide strands comprising the same or substantially the same (i) binding pool targets or (ii) digital signatures, wherein a digital signature of a polypeptide strand is derived from the presence or absence of binding pool targets in the polypeptide strand.

5. The method of claim 1, wherein the optically resolvable distance is about 0.5 micron or greater.

6. The method of claim 1, wherein the solid support is selected from the group consisting of a bead and a porous medium.

7. The method of claim 6, wherein the porous medium is selected from the group consisting of glass and plastic.

8. The method of claim 1, wherein the presence or absence of a plurality of binding pool targets within a single polypeptide strand to be analyzed is determined.

9. The method of claim 8, wherein at least one of the binding pool targets comprises a single amino acid.

10. The method of claim 8, wherein at least one of the binding pool targets comprises a single modified amino acid.

11. The method of claim 10, wherein the single modified amino acid is a glycosylated amino acid.

12. The method of claim 11, wherein the glycosylated amino acid comprises a glycosyl moiety selected from the group consisting of an N-linked glycosyl moiety and an O-linked glycosyl moiety.

13. The method of claim 10, wherein the single modified amino acid is selected from the group consisting of a phosphorylated amino acid, a methylated amino acid, an acylated amino acid, a hydroxyproline and a sulfated amino acid.

14. The method of claim 8, wherein each of the binding pool targets comprises a single amino acid.

15. The method of claim 14, wherein each of the binding pool targets comprises a single modified amino acid.

16. The method of claim 15, wherein the single modified amino acid is a glycosylated amino acid.

17. The method of claim 16, wherein the glycosylated amino acid comprises a glycosyl moiety selected from the group consisting of an N-linked glycosyl moiety and an O-linked glycosyl moiety.

18. The method of claim 15, wherein the single modified amino acid is selected from the group consisting of a phosphorylated amino acid, a methylated amino acid, an acylated amino acid, a hydroxyproline and a sulfated amino acid.

* * * * *